United States Patent
Yang et al.

(10) Patent No.: US 6,869,215 B2
(45) Date of Patent: Mar. 22, 2005

(54) METHOD AND APPARATUS FOR DETECTING CONTAMINANTS IN ION-IMPLANTED WAFER

(75) Inventors: Yu-Sin Yang, Seoul (KR); Sang-Mun Chon, Yongin-si (KR); Sun-Yong Choi, Seongnam-si (KR); Chung Sam Jun, Suwon-si (KR); Kwan-Woo Ryu, Suwon-si (KR); Park-Song Kim, Gwangju-si (KR); Tae-Min Eom, Seongnam-si (KR)

(73) Assignee: Samsung Electrics, Co., LTD, Kyungki-Do (KR)

( * ) Notice: Subject to any disclaimer, the term of this patent is extended or adjusted under 35 U.S.C. 154(b) by 0 days.

(21) Appl. No.: 10/447,104

(22) Filed: May 29, 2003

(65) Prior Publication Data

US 2004/0105486 A1 Jun. 3, 2004

(30) Foreign Application Priority Data

Nov. 28, 2002 (KR) .............................. 10-2002-0074663

(51) Int. Cl.$^7$ ............................................. G01K 11/00
(52) U.S. Cl. .............................. 374/159; 374/5; 374/21
(58) Field of Search ................................. 374/120, 121, 374/5, 57, 45, 44, 159

(56) References Cited

U.S. PATENT DOCUMENTS

| | | | |
|---|---|---|---|
| 4,965,451 A | * | 10/1990 | Solter ............................. 374/5 |
| 5,410,162 A | * | 4/1995 | Tigelaar et al. ................ 374/57 |
| 5,997,175 A | * | 12/1999 | Champetier et al. ......... 374/126 |
| 6,375,348 B1 | * | 4/2002 | Hebb et al. .................. 374/121 |
| 2002/0090746 A1 | * | 7/2002 | Xu et al. ....................... 438/17 |

FOREIGN PATENT DOCUMENTS

| KR | 1998-022840 | 7/1998 |
|---|---|---|
| KR | 1999-018615 | 3/1999 |

* cited by examiner

*Primary Examiner*—Christopher W. Fulton
*Assistant Examiner*—Madeline Gonzalez
(74) *Attorney, Agent, or Firm*—Harness, Dickey & Pierce, P.L.C.

(57) ABSTRACT

A method and apparatus for detecting contaminants in an ion-implanted wafer by annealing and activating the ion-implanted wafer by heating or charging or both, and measuring the thermal wave absorbance generated from the activated wafer.

15 Claims, 8 Drawing Sheets

NORMAL PROCESS

ABNORMAL PROCESS

METHOD AND APPARATUS FOR DETECTING CONTAMINANTS IN ION-IMPLANTED WAFER

RELATED APPLICATION

This U.S. nonprovisional patent application claims priority under 35 U.S.C. § 119 of Korean Patent Application 2002-74663 filed on Nov. 28, 2002, the entire contents of which are hereby incorporated by reference.

FIELD OF THE INVENTION

The present invention relates to a method and an apparatus for detecting contaminants in an ion-implanted wafer, and more particularly to a method and an apparatus for detecting metal contaminants implanted into a wafer with ions during an ion implantation process.

DESCRIPTION OF THE RELATED ART

Generally, an ion implantation method and a diffusion method have been developed for doping impurities into a wafer. The diffusion method has been widely used since the early 1970's. However, the ion implantation method has been currently used for doping the impurities into the wafer because the diffusion method has the following disadvantages. First, it is difficult to control impurity concentration at a shallow concentration level when the impurities are doped into the wafer. Second, it is difficult to control the junction depth of an ion-implanted wafer using the diffusion method. Third, an impurity diffusion area formed in a wafer becomes larger than a desired impurity diffusion area because the impurities previously implanted into the wafer are horizontally and vertically diffused when the diffusion process is executed at a high temperature.

Implantation methods compensate those disadvantages of the diffusion method and also reduce or prevent the impurities from being injected into an undesired region of the wafer by utilizing a photoresist film as a mask. Additionally, impurities doped using an ion implantation method have better uniformity than those doped by a diffusion method. As a result, an ion implantation method has been used in semiconductor fabricating processes. The appliances for executing ion implantation methods have been developed to generate a high energy and a beam current.

Ion implantation methods can be employed for several processes in semiconductor technology, for example, the fabrication of a metal oxide semiconductor (MOS) transistor. As for the fabrication of a MOS transistor, an ion implantation method can:

control a threshold voltage in a field region of the wafer;

form a channel beneath a gate region;

control a threshold voltage beneath the gate region; and form a source region and a drain region of the MOS transistor.

In addition, an ion implantation method may be employed to form a resistance, an emitter, or a base of a bipolar transistor.

Conventional ion implantation apparatus for performing ion implantation method includes a source chamber for generating ions, an analyzer for selecting ions implanted into a wafer among the generated ions, an acceleration tube for accelerating the selected ions so that the accelerated ions are implanted into the wafer at a desired depth, a beam focusing apparatus for focusing the accelerated ion beams, a beam scanning plate for changing the direction of the ion beam in upward, downward, left and right directions, a neutral beam trap for removing neutral beams included in the ion beams, an implantation chamber for implanting the ions into the wafer, and a vacuum device for providing a vacuum for the above-mentioned elements.

After the ions (impurities) are implanted into the wafer by the ion implanting apparatus, thermal wave absorbance and sheet resistance are measured in order to estimate whether or not the ions are properly implanted into the wafer.

Thermal wave absorbance may be measured by using a laser beam generated from a gas mixture of argon and helium, or a laser beam generated from neon. Thermal wave absorbance is a quantitative value that indicates the damage of the wafer from the laser beam. Thermal wave absorbance increases in proportion to the amount of implanted ions and energy. When a laser beam is irradiated onto a portion of the wafer, the damage of the wafer is obtained from the reflectivity of the laser beam reflected from the wafer, and the amount of the implanted ions is measured from the quantitative thermal wave absorbance according to the obtained damage of the wafer.

As described above, when the amount of the impurities is measured by using a laser beam, a reference wafer is fabricated by implanting the ions such that the reference wafer is in a specific band of thermal wave absorbance. The amount of impurities implanted into another wafer is measured in comparison with the reference wafer.

Korean Laid Open Patent Publication No. 1999-018615 discloses a method for fabricating a reference wafer to measure the amount of ions implanted into a wafer. According to the Korean Laid Open Patent Publication No. 1999-018615, after an oxide film is formed on the wafer, ions are implanted into the wafer in a predetermined thermal wave band. Subsequently, the wafer including the implanted ions is annealed for approximately 10 to 15 minutes at a temperature of approximately 120 to 200° C.

While the ion implantation apparatus is normally operated, the sheet resistance of the ion-implanted wafer should be periodically checked so as to determine whether or not the ion implantation apparatus is continuously used. Additionally, after elements of the ion implantation apparatus, which can affect the ion implantation process, are equipped, the sheet resistance of the ion-implanted wafer may be checked.

FIG. 1 is a flowchart illustrating a method for determining an ion implanting process according to Korean Laid Open Patent Publication No. 1998-022840.

Referring to FIG. 1, ions are implanted into a bare wafer in the step ST1. At that time, damage may be caused to the surface of the ion-implanted wafer due to the implanted ions. This damage is measured using the thermal wave method in the step ST2, thereby obtaining a sheet resistance corresponding to the measured thermal wave.

As described above, after the ion-implanted wafer is annealed, metallic contaminants implanted into the wafer are detected. When the thermal wave absorbance generated from the metallic contaminants (namely, a contamination level) is high, the metallic contaminants are advantageously detected using the conventional method. However, if the thermal wave absorbance generated from the metallic contaminants is low, the metallic contaminants may not be adequately detected using the conventional method because the thermal wave absorbance generated from the minute metallic contaminants is small since an amorphous silicon wafer including implanted the ions is converted into a crystalline silicon wafer through the annealing process.

SUMMARY OF THE INVENTION

In an exemplary embodiment, the present invention is directed to a method for detecting contaminants in an ion-implanted wafer.

In another exemplary embodiment, the present invention is directed to an apparatus for detecting contaminants in an ion-implanted wafer.

In another exemplary embodiment, the present invention is directed to a method for detecting contaminants in an ion-implanted wafer, where an amorphous wafer including implanted ions is converted into a crystalline wafer by an annealing process. After the crystalline wafer is activated by applying heat and/or a charge, thermal wave absorbance generated from the activated wafer is measured to detect contaminants in the wafer.

In another exemplary embodiment, the present invention is directed to an apparatus for detecting contaminants in an ion-implanted wafer which includes an first stage for mounting a crystalline wafer thereon, activating means for activating the crystalline wafer, transferring means for transferring the activated wafer, a second stage for receiving the activated wafer, and thermal wave measurement means for measuring a thermal wave absorbance generated from the activated wafer. Ions are implanted into the crystalline wafer, and then the crystalline wafer is annealed.

According to exemplary embodiments of the present invention, the crystalline wafer is activated by applying heat and/or a charge thereto. Therefore, the thermal wave absorbance generated from the activated wafer is measured such that the low level of contaminants in the wafer can be detected.

BRIEF DESCRIPTION OF THE DRAWINGS

The present invention will become readily apparent by from the description of the exemplary embodiments that follow, with reference to the attached drawings in which.

DETAILED DESCRIPTION OF THE EXEMPLARY EMBODIMENTS

Hereinafter, exemplary embodiments of the present invention will be described in detail with reference to accompanying drawings. The same reference labels will be used throughout the figures to denote similar components.

Figure 1:
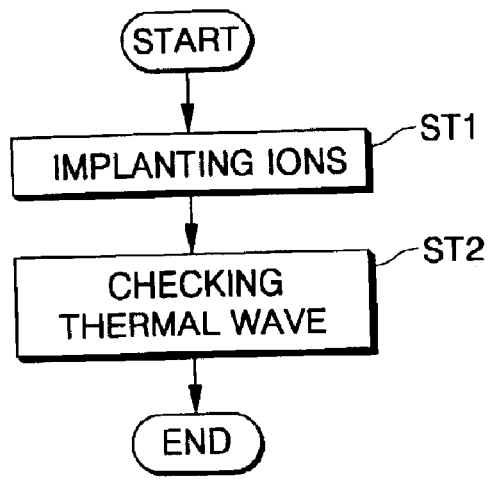
FIG. 1 is a flowchart illustrating a conventional method for detecting contaminants in a wafer.
Figure 2:
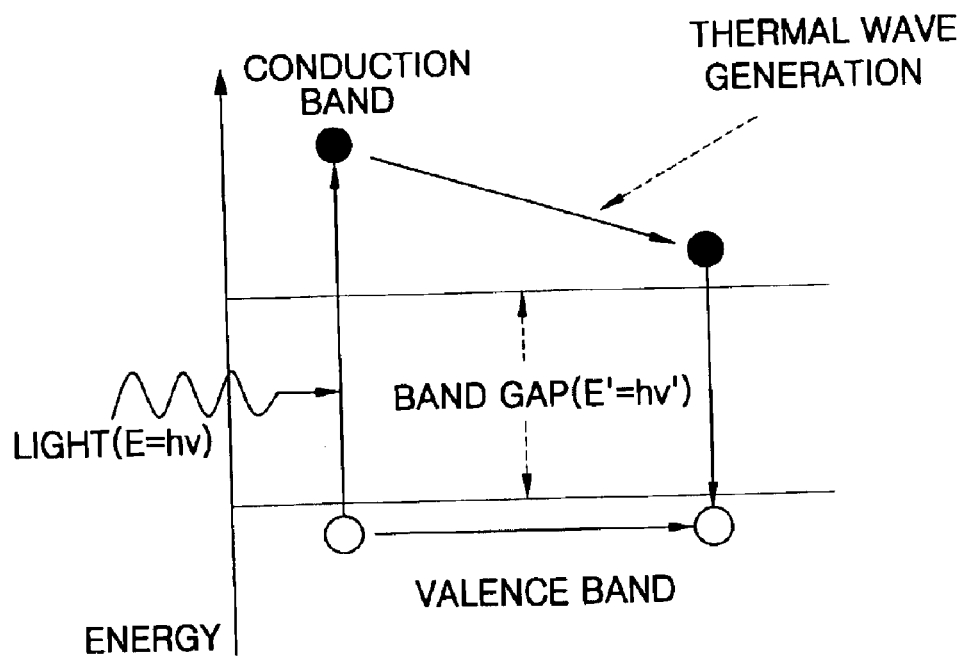
FIG. 2 is a graph illustrating the principle of a thermal wave generation from an ion-implanted wafer.
Figure 3A:
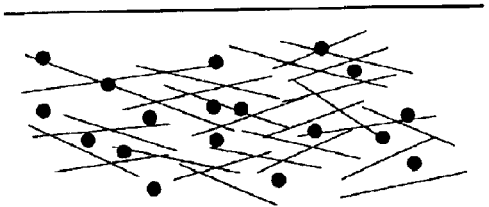
FIGS. 3A and 3B are schematic plane and cross-sectional views illustrating the level of contaminants dispersion in accordance with a normal ion-implanted wafer and an abnormal ion-implanted wafer, respectively.
Figure 3A:
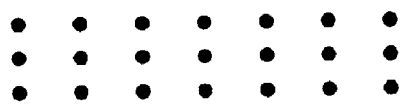
Figure 3B:
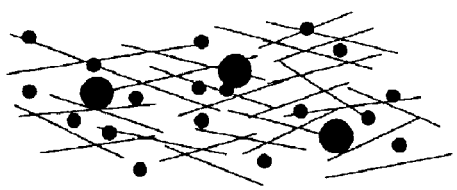
Figure 3B:

FIG. 2 is a graph illustrating the principle of a thermal wave generation from an ion-implanted wafer, and FIGS. 3A and 3B are schematic plane and cross-sectional views illustrating the level of contaminants dispersion in accordance with a normal ion-implanted wafer and an abnormal ion-implanted wafer, respectively.

First, the principle for generating the thermal wave from an ion-implanted wafer is briefly described. Referring to FIG. 2, when a first energy E (wherein, E=hv) greater than a second energy E' (wherein, E'=hv') in a band gap is applied to a bare wafer, an electron positioned at a valence band is migrated to a conduction band such that an electron hole is formed in the valence band. To begin the migration of the electrons, the frequency v of the incident light should be greater than the frequency v' of the band gap between the conduction and the valence bands. The migrated electron moves to the lowermost of the conduction band while the energy of the electron is reduced. At that time, the energy loss of the electron is converted into heat such that a thermal wave is generated from the wafer.

In accordance with the above-described principle of the thermal, the thermal wave generated from the ion-implanted wafer is absorbed into the wafer. The ion-implanted wafer has amorphous phase due to the damage caused by an ion implantation process. The amorphous phased ion-implanted wafer serves as the main source of the thermal wave absorbance.

However, when the amorphous phased wafer is annealed, the amorphous phased wafer is converted into a crystalline wafer. The thermal wave absorbance of the crystalline wafer is nearly identical to that of the bare wafer. Namely, when the amorphous wafer is changed into the crystalline wafer by an annealing process, the thermal wave absorbance generated from the crystalline wafer is reduced.

Referring to FIG. 3, when metallic contaminants are implanted into the wafer with the ions, the metallic contaminants have a small affect on the thermal wave absorbance because the amorphous phased wafer acts as the main source of the thermal wave absorbance as described above. That is, the thermal wave absorbance generated from the metallic contaminants in the amorphous wafer is small.

However, after the annealing process is executed, the amorphous wafer is changed into the crystalline wafer so that the influence of the amorphous wafer relative to the thermal wave absorbance may be decreased. On the other hand, the influence of the metallic contaminants relative to the thermal wave absorbance may be increased. Therefore, when the annealing process is performed, the thermal wave absorbance generated from the metallic contaminants becomes high, thereby sufficiently measuring the contamination of the ion-implanted wafer.

When the contamination degree of the wafer is high, the difference in the thermal wave absorbance between a normal region and a contaminated region on the wafer becomes great. When the contamination degree of the wafer is low, the difference in the thermal wave absorbance between the normal and the contaminated regions on the wafer becomes small. Therefore, the metallic contaminants in the wafer can be barely detected.

In order to detect the metallic containments when the contamination of the wafer is low, exemplary embodiments the method and apparatus of the present invention can exhibit the difference in the thermal wave absorbance between the normal and the contaminated regions of the wafer for detecting contaminants in an ion-implanted wafer.

Figure 4:
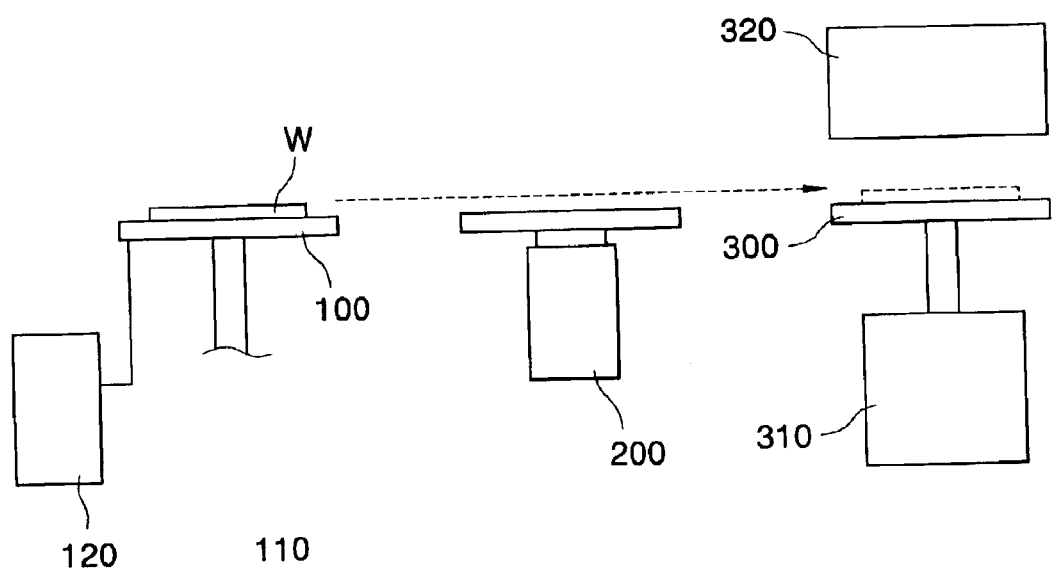
FIG. 4 is a schematic cross-sectional view illustrating an apparatus for detecting contaminants in an ion-implanted wafer according to an exemplary embodiment of the present invention.
Figure 5:
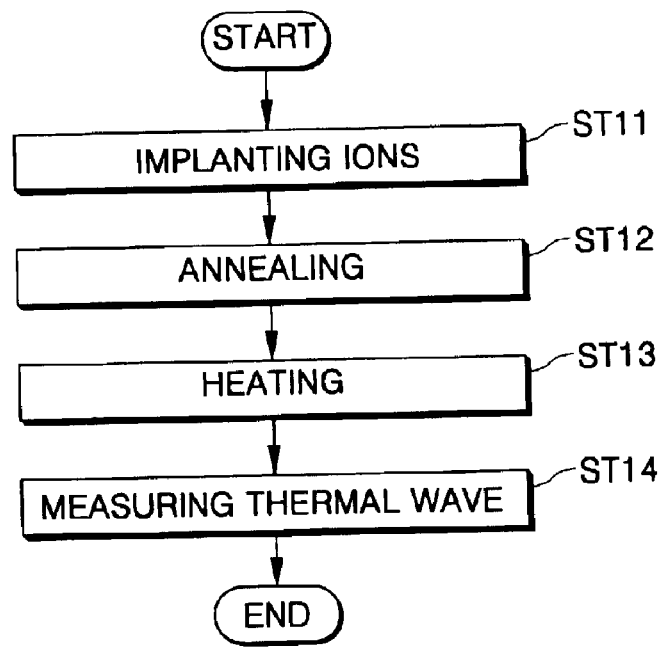
FIG. 5 is a flowchart illustrating an exemplary method for detecting contaminants in the ion-implanted wafer employing the apparatus in FIG. 4.

FIG. 4 is a schematic cross-sectional view illustrating an apparatus for detecting contaminants in an ion-implanted wafer according to an exemplary embodiment of the present invention and FIG. 5 is a flowchart illustrating an exemplary method for detecting contaminants in the ion-implanted wafer by employing the apparatus in FIG. 4.

Referring to FIG. 4, a detecting apparatus of an exemplary embodiment of the present invention includes a first stage 100 on which a wafer W is disposed. The wafer W is a crystalline wafer converted from an amorphous wafer after an annealing process, wherein the amorphous wafer is produced by an ion implantation process.

A heater 120 applies heat to the first stage 100 in order to activate the crystalline wafer W. The activated wafer W is disposed on a second stage 300 by a transferring part 200. The second stage 300 is rotated by a motor 310. A thermal wave measurement member 320 is located over the second stage 300. The thermal wave measurement member 320 can measure the thermal wave absorbance generated from desired regions of the activated wafer W because the activated wafer W is rotated via the motor 310.

An exemplary method for detecting contaminants in the ion-implanted wafer will be explained by employing the detecting apparatus of the exemplary embodiments FIGS. 4 and 5.

Referring to FIG. 5, ions are implanted into a bare wafer W so that the bare W is changed into an amorphous wafer W in step ST11.

In step ST12, the amorphous wafer W is changed into a crystalline wafer W by an annealing process.

After the crystalline wafer W is disposed on the first stage 100, the heater 120 provides heat to the first stage 100 such that the crystalline wafer W is changed into an activated wafer W in step ST13. At that time, the activated wafer W is heated, at an exemplary temperature of approximately 50 to 300° C., more preferably approximately 150° C.

Figure 10:
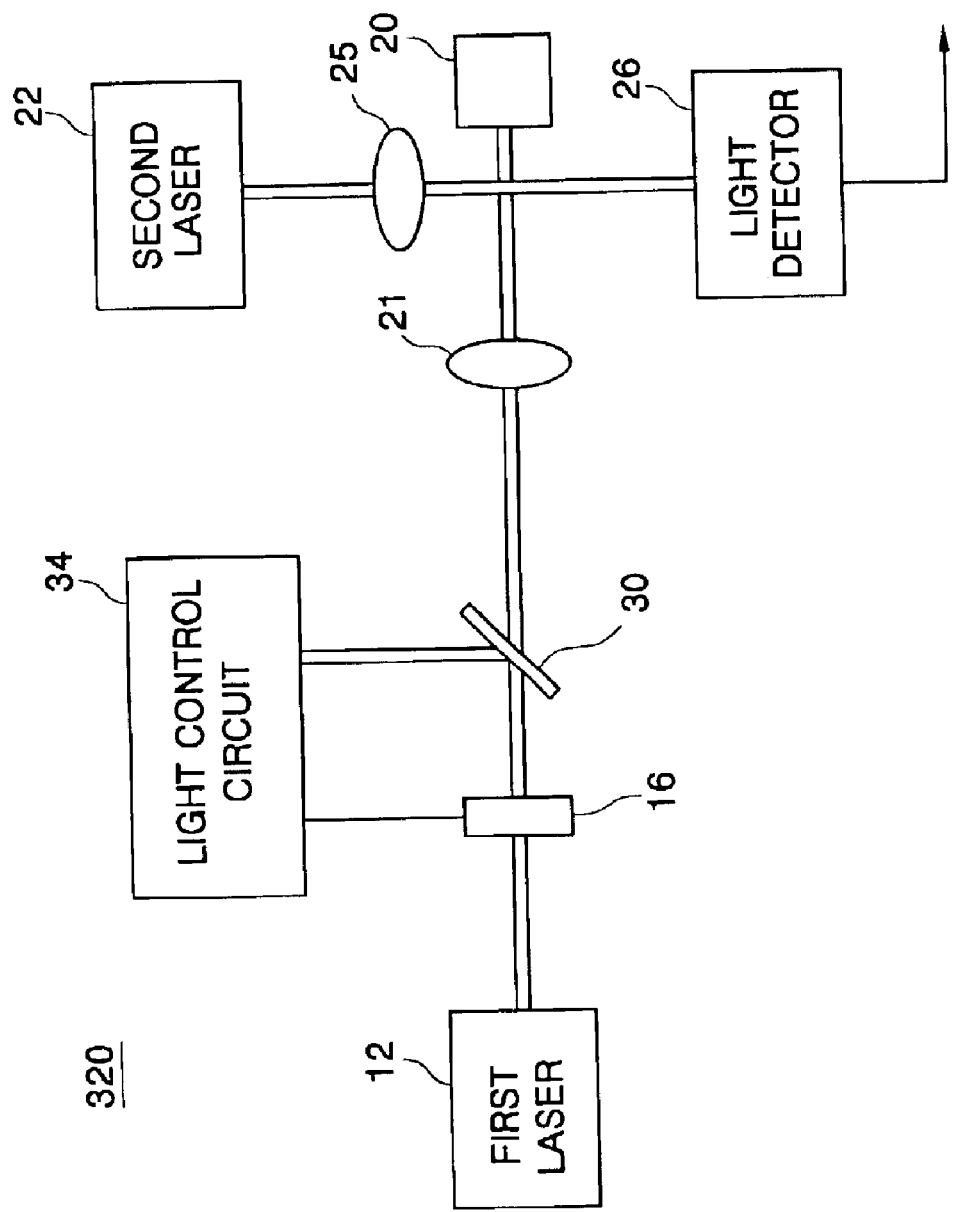
FIG. 10 is a block diagram illustrating a thermal wave measurement member that may be employed in exemplary embodiments of the present invention.

Then, the activated wafer W is transferred to the second stage 300 by the transferring part 200. The thermal wave measurement member 320 measures the thermal wave absorbance generated from the activated wafer W in step ST14. In this case, the difference in the thermal wave absorbance between the normal and the contaminated regions on the wafer W are larger because the wafer W is activated by the heat provided from the heater 120. Thus, the contamination of the wafer W can be more accurately detected. The thermal wave measurement member 320 is well known to those skilled in the art. FIG. 10 is a block diagram illustrating a thermal wave measurement member that can be employed in the exemplary embodiment of the present invention. Referring to FIG. 10, the thermal wave measurement member 320 has a first laser 12, and a second laser 22. The first and the second lasers 12 and 22 are perpendicularly or substantially perpendicular to each other.

An object 20 is located at the point at which the two laser beams generated from the first and the second lasers 12 and 22 intersect. A modulator 16, a mirror 30, and a first lens 21 are serially disposed between the object 20 and the first laser 12. A light control circuit 34 is disposed between the modulator 16 and the mirror 30, and a second lens 25 is located in front of the second laser 22. A light detector 26 for detecting the two laser beams is positioned adjacent to the object 20.

The thermal wave measurement member 320 having the above-mentioned construction can be employed for the detecting apparatus of exemplary embodiments of the present invention. Additionally, other thermal wave measurement members having different constructions can be employed instead of or in conjunction with the thermal wave measurement member described above as a detecting apparatus for executing the method for detecting the contaminants in the wafer in accordance exemplary embodiments of the present invention.

Figure 6:
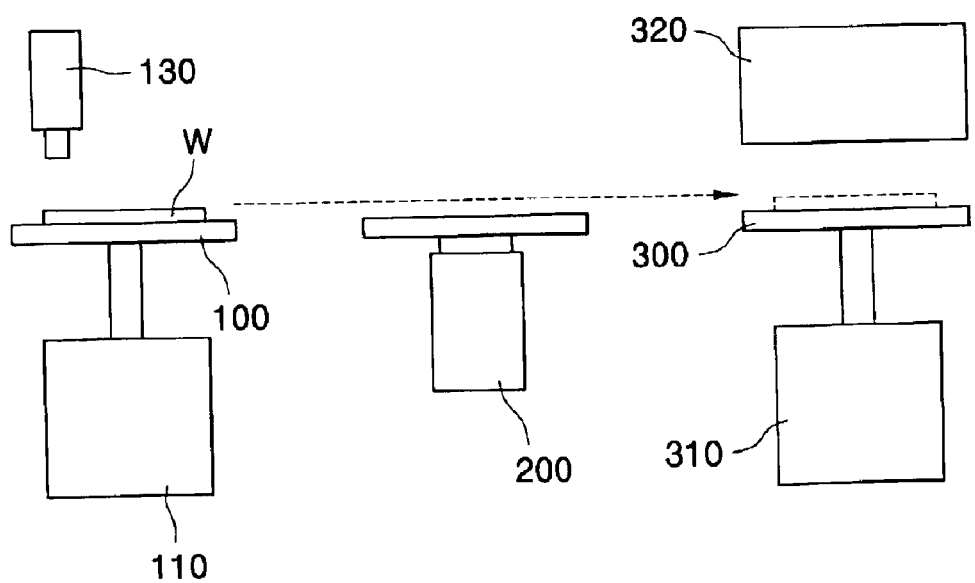
FIG. 6 is a schematic cross-sectional view illustrating an apparatus for detecting contaminants in an ion-implanted wafer according to another exemplary embodiment of the present invention.
Figure 7:
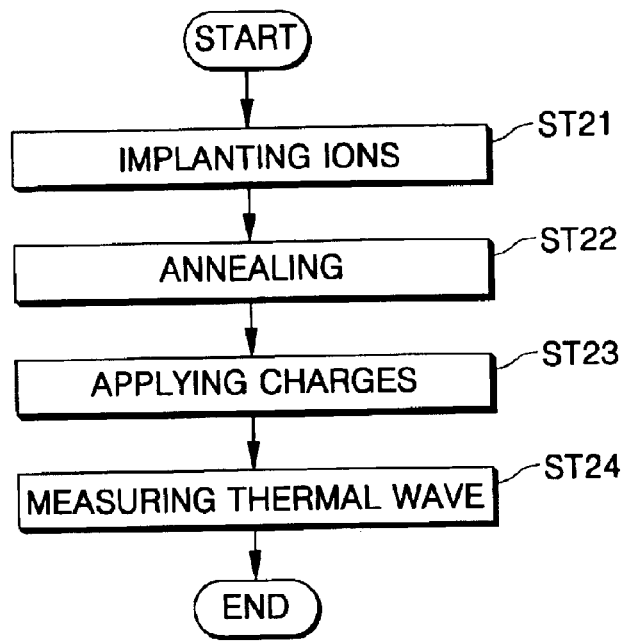
FIG. 7 is a flowchart illustrating an exemplary method for detecting contaminants in an ion-implanted wafer employing the apparatus in FIG. 6.

FIG. 6 is a schematic cross-sectional view illustrating an apparatus for detecting contaminants in an ion-implanted wafer according to another exemplary embodiment of the present invention, and FIG. 7 is a flowchart illustrating a method for detecting contaminants in an ion-implanted wafer by employing the apparatus in FIG. 6.

Referring to FIG. 6, a detecting apparatus of an exemplary embodiment includes a first stage 100 on which a wafer W is disposed. In this case, the wafer W is a crystalline wafer converted from an amorphous wafer after an annealing process, wherein the amorphous wafer is produced by an ion implantation process.

The first stage 100 is rotated via a motor 110, and a charge applying member 130 is positioned over the first stage 100 where the wafer W is positioned. Charges are generated from the charge applying member 130, and then applied to the wafer W to activate the crystalline wafer W. The charge applying member 130 may apply the charges to desired regions of the activated wafer W because the first stage 100 is rotated by the motor 110.

The activated wafer W is disposed on a second stage 300 by a transferring part 200. The second stage 300 is rotated via a motor 310.

A thermal wave measurement member 320 is located over the second stage 300. The thermal wave measurement member 320 measures the thermal wave absorbance generated from desired regions of the activated wafer W because the activated wafer W disposed on the second stage 300 is rotated by the motor 310.

An exemplary method for detecting contaminants in an ion-implanted wafer by employing the detecting apparatus according the exemplary embodiments of the present invention will be described in detail with reference to FIGS. 6 and 7.

Referring to FIG. 7, ions are implanted into a bare wafer W to change the bare wafer W into an amorphous wafer W in step ST21. In step ST22, the amorphous wafer W is changed into a crystalline wafer W by an annealing process.

After the crystalline wafer W is disposed on the first stage 100, the charge applying member 130 applies charges to the crystalline wafer W such that the crystalline wafer W is changed into an activated wafer W in step ST23. Exemplary charges are applied to the wafer W by approximately $1.0 \times 10^{12}$ to $1.0 \times 10^{14}$ C/cm$^2$ or more preferably approximately $2.0 \times 10^{13}$ C/cm$^2$.

The activated wafer W is transferred to the second stage 300 by the transferring part 200. In step ST14, the thermal wave measurement member 320 measures the thermal wave absorbance generated from the activated wafer W. At that time, the difference in the thermal wave absorbance between the normal and the contaminated regions on the wafer W increases because the wafer W is activated with charge. Thus the contamination of the wafer W can be more accurately detected.

Figure 8:
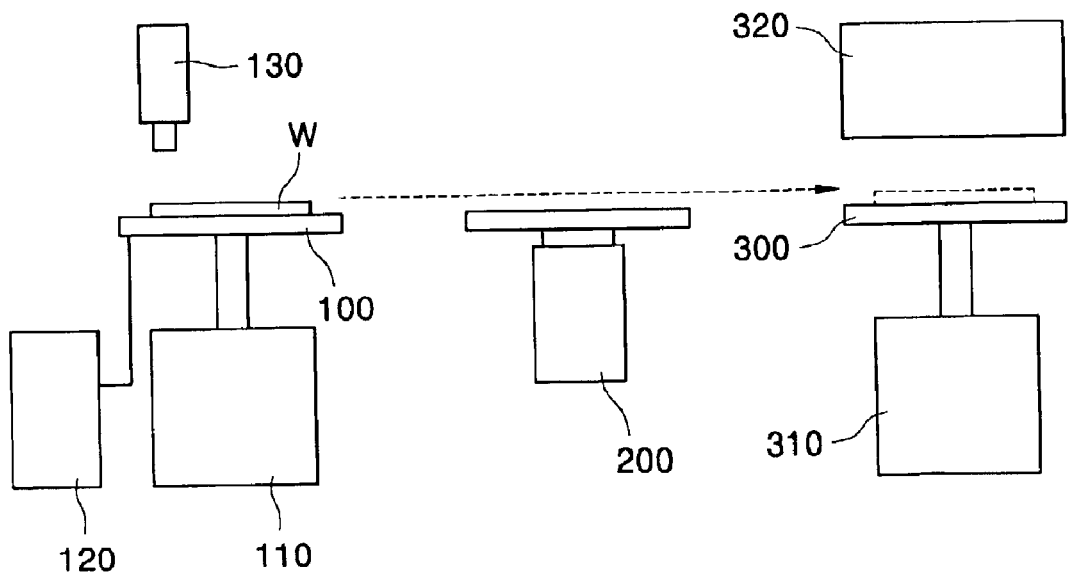
FIG. 8 is a schematic cross-sectional view showing an apparatus for detecting contaminants in an ion-implanted wafer according to another exemplary embodiment of the present invention.
Figure 9:
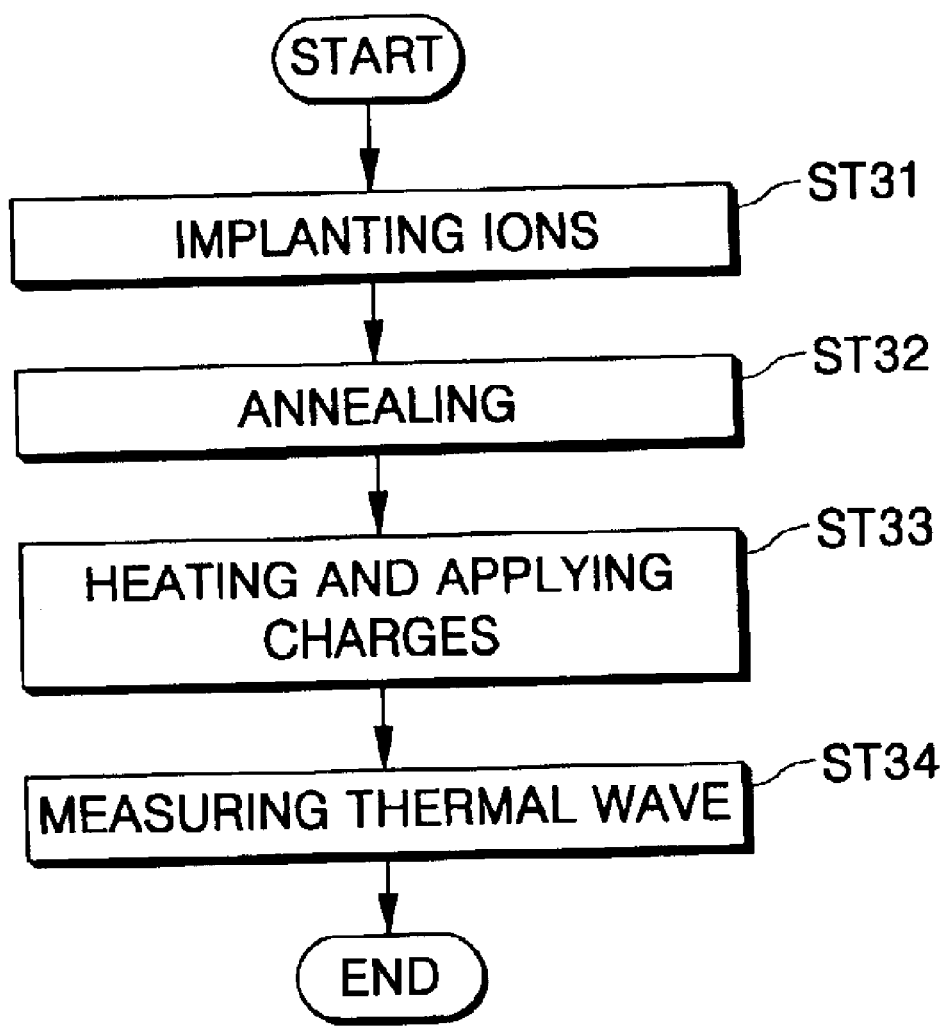
FIG. 9 is a flowchart illustrating an exemplary method for detecting contaminants in an ion-implanted wafer employing the apparatus in FIG. 8.

FIG. 8 is a schematic cross-sectional view showing an apparatus for detecting contaminants in an ion-implanted wafer according to an exemplary embodiment of the present invention, and FIG. 9 is a flowchart illustrating an exemplary method for detecting contaminants in an ion-implanted wafer by employing the apparatus in FIG. 8.

Referring to FIG. 8, a detecting apparatus in accordance with an exemplary embodiment includes a first stage 100 where a wafer W is disposed. The wafer W is a crystalline wafer converted from an amorphous wafer after an annealing process, wherein the amorphous wafer is produced by an ion implantation process.

A charge applying member 130 is positioned over the first stage 100. The charge applying member 130 can applying charges to desired regions of the activated wafer W while the first stage 100 is rotated by the motor 110.

A heater 120 provides heat to the first stage 100 so that the heat and the charges activate the crystalline wafer W.

The activated wafer W is disposed on a second stage 300 by a transferring part 200. The second stage 300 rotates by another motor 310. A thermal wave measurement member 320 is located over a second stage 300. The thermal wave measurement member 320 measures the thermal wave absorbance generated from desired regions of the activated wafer W since the activated wafer W is disposed on the second stage 300 which can be rotated by the motor 310.

An exemplary method for detecting contaminants in the ion-implanted wafer by employing the detecting apparatus in accordance with exemplary embodiments of the present invention will be described in detail reference to FIGS. 8 and 9.

Referring to FIG. 9, ions are implanted into a bare wafer W such that the bare wafer W is changed into an amorphous wafer W in step ST31. Then, the amorphous wafer W is changed into a crystalline wafer W by an annealing process in step ST32.

After the crystalline wafer W is disposed on a first stage 100, the charge applying member 130 applies charges to the crystalline wafer W. In this case, the charges are applied to the wafer W at approximately $1.0 \times 10^{12}$ to $1.0 \times 10^{14}$ C/cm$^2$, preferably by approximately $2.0 \times 10^{13}$ C/cm$^2$. Simultaneously, the heater 120 provides heat to the first stage 100. At that time, the wafer W is activated at a temperature of approximately 50 to 300° C., preferably at a temperature of approximately 150° C. Thus, the crystalline wafer W is changed into an activated wafer W by the heat and the charges in step ST33.

The activated wafer W is transferred to a second stage 300 by the transferring part 200. In step ST34, the thermal wave measurement member 320 measures the thermal wave absorbance generated from the activated wafer W. The difference in the thermal wave absorbance between the normal and the contaminated regions of the wafer W is increased because the wafer W is activated with the heat and the charges. Therefore, the contamination of the wafer W can be more accurately detected.

Figure 11:
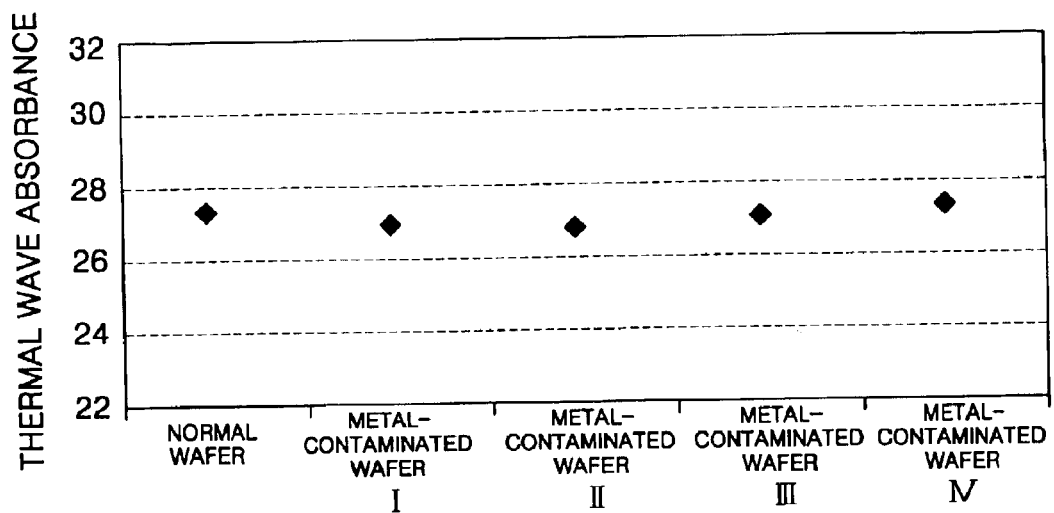
FIG. 11 is a graph illustrating thermal wave absorbances generated from a normal and four abnormal wafers including minute contaminants in accordance with exemplary embodiments of the present invention.
Figure 12:
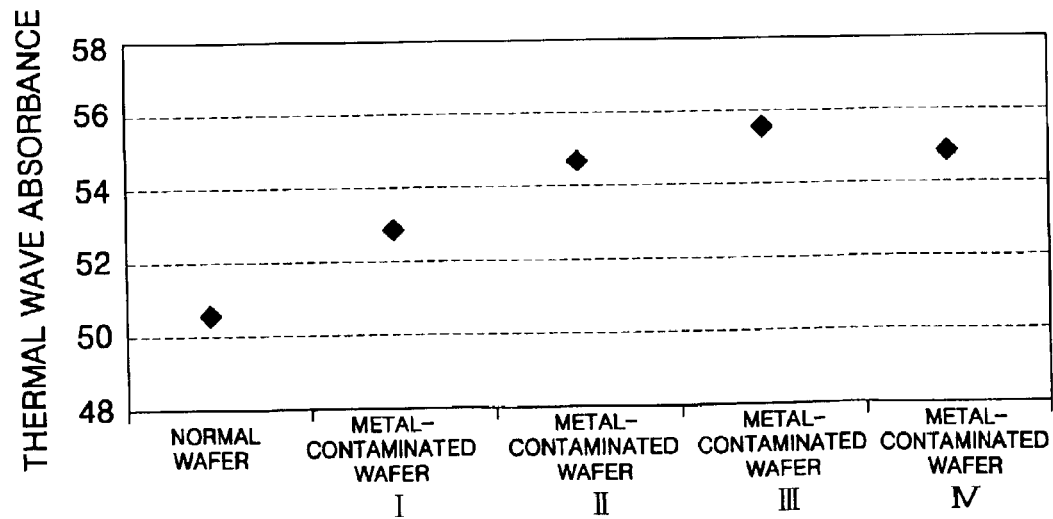
FIG. 12 is a graph illustrating thermal wave absorbances generated from the normal and the four abnormal wafers after heat and charges are applied to all the wafers in accordance with exemplary embodiments of the present invention.

FIG. 11 is a graph illustrating thermal wave absorbances generated from a normal and four abnormal wafers including minute contaminants and FIG. 12 is a graph illustrating thermal wave absorbances generated from the normal and the four abnormal wafers after heat and charges are applied to all the wafers.

At first, phosphorus ions are implanted into five wafers by approximately $1 \times 10^{14}$ numbers/cm$^2$ with the energy of approximately 800 kV. Metallic contaminants are implanted into four wafers I to IV among the five wafers with the phosphorous ions. On the other hand, the metallic contaminants are not implanted into the remaining one wafer. At that time, the metallic contaminants are implanted into the wafer I by approximately $4 \times 10^{10}$ numbers/cm$^2$, and the metallic contaminants are implanted into the wafer 11 by approximately $6 \times 10^{10}$ numbers/cm$^2$. In addition, the metallic contaminants are implanted into the wafer III by approximately $1 \times 10^{11}$ numbers/cm$^2$, and the metallic contaminants are implanted into the wafer IV by approximately $8 \times 10^{10}$ numbers/cm$^2$.

Next, all the wafers are annealed at the temperature of approximately 850° C. The thermal wave absorbances generated from the all wafers were measured. The measurement results are shown in FIG. 11.

As shown in FIG. 11, the difference of the thermal wave absorbances between the normal wafer and the minutely contaminated wafers I to IV was hardly recognized. That is, the minute contaminants could not be detected in the previously contaminants-treated wafers because the thermal wave absorbances generated from the contaminated wafers I to IV were nearly identical to the thermal wave absorbance of the normal wafer. Furthermore, though the contaminants were differently included in the contaminated wafers I to IV, the difference of the thermal wave absorbances between the contaminated wafers I to IV was also hardly identified.

On the other hand, an exemplary method of the present invention was applied to the normal wafer and the contaminated wafers I to IV, namely, after the heat and the charges were applied to the normal wafer and the contaminated wafers I to IV under the conditions identical to the above-mentioned conditions, the thermal wave absorbances generated from all the wafers were measured at the temperature of approximately 150° C. when the charges were applied all the wafers by approximately $2.0 \times 10^{13}$ C/cm$^2$. As seen from the measurement results of FIG. 12, the thermal wave absorbances generated from the contaminated wafers I to IV were different from that of the normal wafer. In particular, the difference in the thermal wave absorbance between the contaminated wafers I to IV was increased.

As described above, the contamination degree of a lightly contaminated wafer can be detected by measuring the thermal wave absorbance generated from the wafer activated with the heat and/or the charges.

Although exemplary embodiments of the present invention described above illustrate two stages, one stage or more than two stages could also be utilized without varying from the spirit and scope of the present invention.

In exemplary embodiments of the present invention, the amorphous wafer is produced by implanting ions into a bare wafer. However, the amorphous wafer may be produced by other techniques known to one of ordinary skill in the art. In exemplary embodiments of the present invention, the crystalline wafer is formed by annealing an amorphous wafer. However, other processes, know by one of ordinary skill in the art could be utilized to create the crystalline wafer.

In exemplary embodiments of the present invention, the activated wafer is formed by heating a crystalline wafer, by charging a crystalline wafer, or by simultaneously heating and charging a crystalline wafer. However, the activated wafer may be produced by other techniques known to one of ordinary skill in the art, including the application of other phenomenon other than heat or charge, either simultaneously or sequentially, and if sequentially, in any order.

Although the present invention has been particularly shown and described with reference to the exemplary embodiments described above, it will be understood by those skilled in the art that these exemplary embodiments do not limit the present invention, and that various changes in form and details may be made without departing from the spirit and scope of the invention as defined by the appended claims.

What is claimed is:

1. A method comprising:

converting a wafer into a crystalline wafer by annealing the wafer;

activating the crystalline wafer thereby forming an activated wafer;

measuring thermal wave absorbance generated from the activated wafer; and detecting contaminants in the crystalline wafer based on the measured thermal wave absorbance.

2. The method of claim 1, wherein the crystalline wafer is activated by heating.

3. The method of claim 2, wherein the heating is at a temperature from 50 to 300° C.

4. The method of claim 1, wherein the crystalline wafer is activated by applying at least one charge thereto.

5. The method of claim 4, wherein the at least one charge is in a range from $1.0 \times 10^{12}$ to $1.0 \times 10^{14}$ C/cm$^2$.

6. The method of claim 1, wherein the crystalline wafer is activated by simultaneously heating the crystalline wafer and applying at least one charge to the crystalline wafer.

7. The method of claim 6, wherein the crystalline wafer is heated at a temperature of approximately 50 to 300° C. and the at least one charge is in a range of approximately $1.0 \times 10^{12}$ to $1.0 \times 10^{14}$ C/cm$^2$.

8. The method of claim 1, wherein the crystalline wafer is formed by sequentially heating the crystalline wafer and applying at least one charge to the crystalline wafer.

9. A contaminant detecting apparatus for performing the method of claim 1.

10. An apparatus comprising:

first stage for supporting a crystalline wafer which has been ion-implanted and annealed;

an activator activating the crystalline wafer disposed on the first stage means to form an activated wafer;

second stage supporting the activated wafer;

transfer device for transferring the activated wafer onto the second stage;

thermal wave measurement means for measuring a thermal wave absorbance generated from the activated wafer disposed on the second stage; and detecting contaminants in the crystalline wafer based on the measured thermal wave absorbance.

11. The apparatus of claim 10, wherein the activator includes a heater.

12. The apparatus of claim 10, wherein the activator includes a charge applying member.

13. The apparatus of claim 12, further comprising a motor for rotating the first stage so that the charge applying member applies charges to desired regions of the wafer.

14. The apparatus of claim 10, further comprising a motor for rotating the second stage.

15. The apparatus of claim 10, wherein the activator includes a heater and a charge applying member.

* * * * *